United States Patent [19]

Kugimiya et al.

[11] 4,333,067
[45] Jun. 1, 1982

[54] CERAMIC TYPE SENSOR DEVICE

[75] Inventors: Koichi Kugimiya, Toyonaka; Fumio Hosomi, Hirakata; Yoshihiro Matsuo, Neyagawa; Tsuneharu Nitta, Katano, all of Japan

[73] Assignee: Matsushita Electric Industrial Co., Ltd., Osaka, Japan

[21] Appl. No.: 130,434

[22] Filed: Mar. 14, 1980

[30] Foreign Application Priority Data

Mar. 20, 1979 [JP] Japan .................................. 54-32688
Jun. 14, 1979 [JP] Japan .................................. 54-75307
Jun. 14, 1979 [JP] Japan .................................. 54-75309

[51] Int. Cl.³ ............................................ H01L 7/00
[52] U.S. Cl. .................................................. 338/34
[58] Field of Search ................ 338/28, 34, 35, 308, 338/309, 22; 73/27; 422/98; 23/232 E; 200/61.03; 340/632

[56] References Cited

U.S. PATENT DOCUMENTS

| 4,001,758 | 1/1977 | Esper et al. | 338/28 X |
| 4,007,435 | 2/1977 | Tien | 338/28 X |
| 4,057,996 | 11/1977 | Firth et al. | 338/34 |
| 4,103,275 | 7/1978 | Diehl et al. | 338/28 X |
| 4,147,513 | 4/1979 | Bienkowski et al. | 73/23 X |
| 4,234,542 | 11/1980 | Romine | 338/34 |

Primary Examiner—C. L. Albritton
Attorney, Agent, or Firm—Stevens, Davis, Miller & Mosher

[57] ABSTRACT

A ceramic sensor device is disclosed which comprises a sensing element of a ceramic material and electric conductors for connection to external circuit which are tightly embedded within a ceramic insulating body. The solid state sensor device having an excellent capability to withstand detrimental conditions such as a high temperature, rapid temperature change and mechanical shocks is provided. The sensor is advantageously used as a temperature sensor, a moisture sensor and a gas sensor for detecting oxidizing and reducing gas. Above all, the sensor is suited as a temperature sensor device for detecting temperature of exhaust gas purifying catalyst used in motor vehicles.

10 Claims, 8 Drawing Figures

CERAMIC TYPE SENSOR DEVICE

The present invention relates to a sensor device and a method for manufacturing the same. More particularly, the invention concerns a sensor device which can be employed under severe environmental conditions such as a high temperature in a range of about 300° C. to about 800° C. or more.

For the sensor device of the type described above, there has been known a temperature sensor device which is adapted to detect the temperature of an exhaust gas purifying catalyst used in motor vehicles. Operation reliability and stability to an appreciable degree has been assured in such sensor. However, the conventional sensors suffer from many drawbacks. For example, manufacturing cost is high. Electric connections are frequently broken at the electric conductors or joint portions (junctions) due to mechanical vibrations and stresses although the vibrations and stresses of the electric conductors are to be supressed at the joint portions by filing voids of the sensor device with heat-resistive inorganic powders. Failures or faults are frequently observed in the electrodes embedded in a sintered ceramic material serving as a temperature sensitive element since a large amount of residual stresses is left in the ceramic material owing to the contraction produced when sintered. Platinum electrodes as required are very expensive, and so forth. Many problems remain to be solved.

An object of the invention is to provide an improved sensor device from which drawbacks or shortcomings of the prior art sensors such as described above are significantly eliminated and which enjoys wide and various applications in addition to the temperature sensor for motor vehicle.

Another object of the invention is to provide an inexpensive sensor device which can be so implemented as to serve as a moisture sensor, a gas sensor with a high reliability and other sensing devices.

In view of the above and other objects which will become more apparent as the description proceeds, there is proposed according to a general aspect of the invention a sensor device as set forth in claim 1.

Now, the invention will be described in detail in conjunction with exemplary embodiments illustrated in the accompanying drawings.

Figure 1:
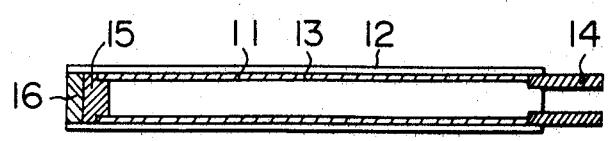
FIG. 1 is a cross-sectional view to show a sensor device according to an embodiment of the invention.

Referring to FIG. 1 which shows in a sectional view of a sensor device according to an embodiment of the invention, the sensor includes an insulating substrate 11 which may be formed of a solid ceramic material, a pair of electrical conductors 13 formed on the insulating substrate 11 and tightly covered by an insulating coat 12, a pair of output terminals 14 provided at one end of the substrate 11 and a sensor element 15 disposed at the other end of the substrate and electrically connected between the pair of electrical conductors 13. The mechanical strength of the sensor structure is assured by the inherent mechanical strength of the ceramic substrate 11. For example, the insulating substrate formed of alumina porcelain having a high density exhibits a deflection strength on the order of 1500 to 2000 Kg/cm$^2$ and does not undergo rupture even when it is dropped against a concrete surface from the height of 1 m. In the following description, exemplary embodiments of the invention applied to high temperature reponsive sensor devices will be described in more concrete terms.

An advantageous structure of the sensor device according to the invention comprises fundamentally a column-like insulating ceramic 11, an insulating ceramic coat 12 covering the column-like or sheet like ceramic substrate, at least two electric conductors 13 interposed between the insulating coat 12 and the ceramic substrate 13, a pair of electrode terminals 14 for external connection which are electrically contacted to exposed ends of the electric conductors 13, respectively, and led outwardly along the surface of the substrate 12 at one end thereof, and a mass 15 of a sensing material (hereinafter referred to as the sensor element). In view of the fact that the sensor element must sometimes be protected from the ambient atmosphere in dependence on the type of temperature sensitive material, a protection film 16 may be deposited over the sensor element 15, as occasion requires. It should be mentioned here that the terminals 14 may be provided at the outer surface of the sheet-like insulating coat 12 without altering the function thereof.

The temperature sensor device of the structure described above may be fabricated in the manner described below. Through a process conventionally employed in the sophisticated ceramic industry, a raw sheet material which is destined to form ultimately the sheet-like insulating coat 12 is prepared and electrically conductive material for constituting the electric conductors 13 is applied to the raw insulating sheet material in a predetermined pattern. Subsequently, appropriate holes for leading the terminals 14 outwardly are formed concurrently with cutting of the raw insulating sheet material in a desired size. At the next step, the raw insulating sheet material thus prepared is tightly wound around a raw column-like material which is destined to form ultimately the column-like insulating substrate 11 so that the electric conductor pattern 13 is interposed between the raw insulating sheet material and the raw column-like material without being accompanied by generation of any bubbles. The shaped assembly thus obtained is then subjected to a firing process at a temperature selected in dependence on the materials as used. When tungsten (W) or a metallic material of Mo-Mn series is used for the electric conductors, the firing treatment is effected in a reducing atmosphere. The temperature for the firing treatment in the former case (i.e. for the conductor of W) contained with high AL$_2$O$_3$ ceramics is higher than about 1650° C., while in the latter case the corresponding temperature should be higher than about 1500° C.

Next, the terminals 14 are formed through a conventional metallizing process. More specifically, when tungsten (W) is used for the electric conductors, the terminals 14 may be welded to the associated conductors 13 by means of a high temperature solder or nickel after the corresponding portions of the conductors 13 have been plated with nickel (Ni). Subsequently, the sensor element 15 is provided at the other end of the sensor sub-assembly thus fabricated. The sensor element 15 may be provided through bonding or welding after the sensor element has been subjected to a firing process and cut in a final dimension. Alternatively, the sensor element 15 may be formed through a flame spraying process, evaporation process or sputtering process thereby to directly attain a rigid bonding which can assure a high reliability. When it is required to protect the sensor element from corrosive action of an ambient gas in which the sensor device is used, the protection film 16 having a reasonable thickness may be formed on the sensor element 15 through a flame spraying.

The high temperature sensor element thus obtained may be used in this state. However, in view of a stabilized characteristic and removal of residual thermal stress, it is preferred that the sensor device as a whole is annealed at a temperature slightly higher than those employed in an actual usage.

For realizing the electric conductors 13, pastes of $MoSi_2$, $LaCrO_3$ or the like may be alternatively used. Further, the conductor material may be applied to the outer surface of the column-like insulating substrate 11 through printing or evaporation process to attain the same effects.

Further in place of using the raw sheet-like material for the insulating coat 12 as described above, a paste of material which forms the insulating protection coat or film 12 when subjected to firing may be deposited around the column-like substrate after the conductor material 13 has been applied through a printing or the like process. As a further alternative, the conductor pattern 13 may be first formed through evaporation or sputtering on the pheripheral surface of the column-like insulating substrate 11 which has been fired and subsequently the sheet-like insulating film 12 is then applied through a similar process to accomplish the sensor device having the same configuration and sensing function as those of the sensors fabricated in the manner described hereinbefore.

For the material destined to form the column-like substrate and the insulating coat, materials such as magnesia and mullite porcelain exhibiting a higher resistance than the sensing element may be used in addition to alumina described hereinbefore. It goes without saying that the column-like insulating substrate and the insulating coat may be formed of different materials so far as they can fully withstand thermal stresses. The temperature sensor element 15 may be formed of hitherto known temperature sensitive material such as spinel oxides, Provskite, zirconia containing oxides or the like. These materials exhibits such temperature-resistance characteristic that the resistance value of $10^{10} \Omega cm$ or more at a room temperature is decreased even to the order of 1 $\Omega cm$ at a temperature of about 1000° C. Further, the resistance varying ratio usually referred to as B constant amounts to 10,000° K. Accordingly, the resistance of the refractory insulating material(s) for forming the column-like substrate and the coat should be sufficiently higher than the resistance of the temperature sensitive material forming the sensor element 15. For example, the resistance of the former material may be 100 times as high as that of the temperature sensitive material. For practical application, only a portion at which the sensor element 15 is disposed is subjected to a high temperature, while the remainder portion will remain at a relatively low temperature. Thus, the resistance of the insulating substrate and coat may be lowered slightly than the value recited above without giving rise to any problem.

It has been found that the protecting action of the sheet-like insulating coat 12 is excellent. In reality, with the insulating coat formed of alumina in the film thickness of 50 $\mu m$, the resistance of the inner electric conductor undergoes substantially no variation even after the continuous exposure to a temperature of 900° C. in air atmosphere for 10,000 hours, as will be hereinafter made apparent from the description of the examples. The porosity of the insulating coat film does not exceed 5% and is lower than 1% in many cases.

By forming the responsive sensor element 15 from a material of $MgCr_2O_4$—$TiO_2$ series, for example, in the manner described hereinbefore, a moisture sensor device having a high reliability can be obtained. Since the sensor device is then operated in the vicinity of a room temperature, an extremely high heat resistance is not required. However, with a view to burn away oil or the like surface pollutants, the sensor element is heated to a temperature in a range of 400° to 500° C. In this case, the conditions similar to those brought about by rapid heating and rapid cooling will prevail to contribute to excellent characteristics of the ceramic sensor device according to the invention. The heater for heating the sensor element can be advantageously realized by an additional electric conductor embedded in the sensor device and having portions of high resistance.

When the sensor element or material is formed of a gas sensitive material such as $SnO_2$, $Fe_3O_4$, $ZnO$ or the like in the manner described hereinbefore, the sensor device can be implemented as a gas sensor device. In this case, the sensor is usually operated at a temperature in a range of 300° to 600° C. It is preferred that heater means is incorporated also in the gas sensor device as in the case of the moisture sensor device.

Figure 2:
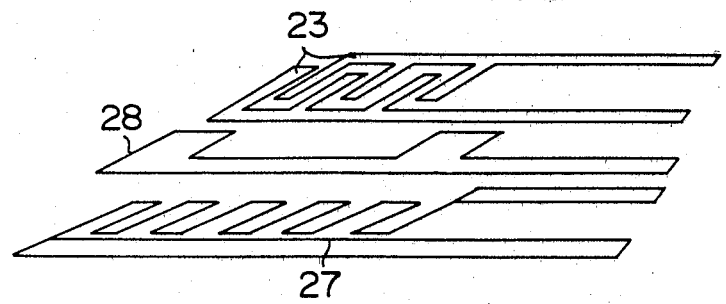
FIG. 2 shows a structure of a sensor device which includes a heater, a control conductor in addition to a pair of electric conductors.

The heater described above may be implemented in a form of a heat generating portion 27 provided immediately below the end portion of an electric conductor 23 of the sensor to be grounded, as is shown in FIG. 2. The heater is electrically insulated from the electric conductor by an insulating material, whereby a temperature control may be effected on the basis of variation in resistance detected through cooperation of the heat generating portion 27 and one of the electric conductors 23. An additional control electrode 28 may be additionally provided to attain the similar effect.

The heater portion may be formed of a same material as the electric conductor so as to have a large length and a restricted cross-sectional area. When the sensor device is imparted with a high porosity so as to be used in an oxidizing gas flow, it is preferred to protect exposed portions of the electric conductors through plating with platinum. It is apparent that the protection film 16 should not be formed with a high density when the sensor is to be used as the gas sensor and the moisture sensor. Rather, it has been found that a film having a high porosity and capable of preventing foreign particles or materials from directly contacting the sensor element to destroy or injure it is more advantageous as the protection film. Such porous protection film may be formed of alumina through plasma flame spraying at a low power of 18 V and 400 A or alternatively through a low speed flame spraying with a high output power of 35 V and 700 A. In the latter case, the target (sensor element) is spaced from the plasma flame nozzle by a distance of 150 mm or more.

The sensor device according to the invention is very advantageous in respect of the reliability and lengthened use life, as will be readily appreciated from the integrated structure and the absence of the voids. The portion of the sensor device which is susceptible to failure is a grounding portion of the sensor element. In the hitherto known sensor devices, remarkable deterioration or damage tends to occur at the expensive electrodes formed of platinum and embedded in the ceramic material constituting the sensor element and failures or faults are often observed at the junctions such as the welded portion of the lead-wires. In contrast, it has been found that the sensor device according to the invention is substantially immune to such deterioration, damage and failure. Further, the hitherto known sensors suffer from many shortcomings such as poor mechanical strength of the embedded electrodes, poor yield, a number of troublesome procedures required due to complicated structure and are expensive. In this invention, the grounding portion of the temperature sensitive element can be realized at a yield of substantially 100% and the number of fabricating steps can be significantly reduced with individual steps being carried out in a simplified manner due to a simple structure of the sensor, involving a significant reduction in manufacturing costs to great advantages.

As a result of an absence in voids in the sensor device, the stability during use is increased. This results because if voids are present within the ceramic material, the output terminals are overheated owing to the increase of heat conductivity by the diffusion of high temperature gases through the voids, or assuming that the voids are sealed therein, a considerably large amount of stresses are applied to the shell of the sensor owing to the expansion and contraction of air in the voids, which in turn induces fatigue from the repetitive use of the sensor.

Further, the heat-resistivity is excellent because of the absence of organic compounds conventionally used.

Figure 3A:
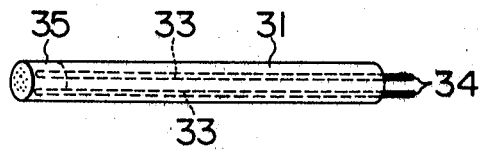
FIGS. 3 to 6 illustrate structures of sensor devices according to further embodiments of the invention.
Figure 3B:
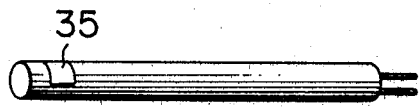
Figure 4:
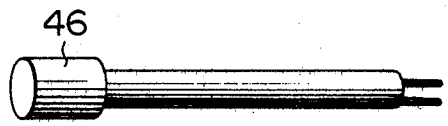

Next, description will be made on another structure of the sensor device according to the invention. Referring to FIG. 3a, a pair of electric conductors 33 which serve also as a pair of terminals are embedded within an insulating ceramic body 31 in an integral form. A sensing element 35 is provided at one exposed end portions of the conductors 33. The insulating body 31 as well as the sensing element 35 may be conveniently realized through the flame spraying described hereinbefore. In order to form the insulating body of a high density (i.e. having a porosity not higher than 5%), a high speed plasma spraying is preferred. In this case, argon gas may be employed as plasma gas and the fusing is effected at a short distance in a range of 30 to 70 mm at the output power of 700 A and 35 V. As a variation of the structure shown in FIG. 3b, the sensing element 35 may be provided at a side of the insulating body 31 to the same effect. Further, a protection film 46 may advantageously be provided to protect the sensing element from detrimental atmosphere as illustrated in FIG. 4, although the temperature sensitivity is somewhat lowered. Particularly, when the sensing element is formed of a material exhibiting a dependency on the partial pressure of oxygen such as a material of zirconia porcelain series, it is necessary to prevent the sensing element from contacting the atmosphere. The porosity of the protection film 46 of the sensor device to this end should be lower than 5%, inclusive, and more preferably lower than 1%, inclusive.

Figure 5:
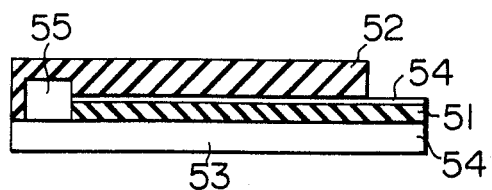

In the following, various modification and variation of the sensor device according to the invention will be described. Referring to FIG. 5, an electrically insulating layer 51 and an electrically conductive layer 54 are successively laminated on a refractory metallic supporting base 53. A sensing element 55 is electrically connected between the metallic supporting base 53 and the upper electrically conductive layer 54. The conductive layer 54 as well as the supporting base 53 serves to act as an output terminal. The sensing element 55 may be provided in a manner shown in FIG. 5 in which the element 55 is contacted to the electrically conductive layer 54 at one end and to the metallic supporting base 53. Alternatively, a corresponding window is formed in the insulating layer 51, whereby the detecting element 55 is connected to the portion of the refractory metallic supporting base 53 exposed through the window and the electrically conductive layer 54. Further, an additional electrically conductive layer is provided to contact the portion of the refractory metallic base exposed, wherein the sensing element is so arranged to be electrically connected to both the additional conductive layer and the conductive layer 54. The sensor device of the structure described above may be manufactured in the manner described below. The insulating layer 51 of $Al_2O_3$, MgO, mullite or the like material, for example, is deposited on a masked surface of the refractory metal base such as Hastelloy through flame spraying process. The thickness of the insulating layer 51 may be in a range of 50 to 200 μm. Next, the electrically conductive layer 54 is formed on the insulating layer 51 through a flame spraying process or by applying and firing an electrically conductive refractory paint. For the electrically conductive material of this kind, platinum, a Nichrome alloy, ruthenium or the like may be used. Tungsten may also be used for forming the electrically conductive material. However, in this case, a protection film will have to be provided, since tungsten is susceptible to oxidization at a high temperature. At the succeeding step, the sensing material for forming the sensing element 55 is applied to the sub-assembly through a flame appraying. For the material to form the sensing element destined to serve as the temperature sensing element, there may be enumerated spinel, Provskite, zirconia containing oxides or the like which have been well known in the art and can be easily applied through the flame spraying. The resistance values of these materials vary from ca. $10^{10}$ Ωcm to 1 Ωcm in dependence on temperature variation from 300° C. to well above one thousand degrees (° C.). Since the resistance value of the temperature sensitive materials enumerated above which is in the order of $10^{10}$ Ωcm or higher at a room temperature is decreased to 1 Ωcm at a temperature of ca. 1000° C., the refractory oxide insulation layer need not have a very high resistance. Further, because the portion subjected to a high temperature is only the portion located in the vicinity of the temperature sensing element, there will arise no problem in practice even when the resistance value of the refractory oxide insulation layer is somewhat small at a low temperature, as described hereinbefore.

It is preferred that those portions of the metallic supporting base 53 and the electrically conductive layer 54 with which the temperature sensitive element 55 is brought into contact is previously plated with platinum or the like thereby to prevent mutual diffusion of elements constituting the base 53, the layer 54 and the temperature sensitive element. Further, it is preferred that the end portion of the sensor device opposite to the temperature sensitive element 55 is realized in a plug-like configuration as shown in FIG. 5 so as to be used as a connector terminal, since then the connecting structure can be simplified without requiring additional electrode terminals or lead wires, while reliability in operation of the device is enhanced. It will be self-explanatory that preparatory treatment such as sand blasting is preferably carried out in precedence to the flame spraying. There are a variety of methods for carrying out the flame spraying. Among them, the plasma injection process is preferred for the reasons that the process can be accomplished in a short time without involving any significant temperature rise in the sensor device, while assuring an improved characteristics in respect of the density of the fused mass.

When the sensor device is intended for use in such unfavorable environmental condition in which the sensitive element and the electrically conductive layer are subjected to corrosion or erosion, the insulation film 52 should be formed through the flame spraying so as to cover the sensitive element and the electrically conductive layer for protecting them from the corrosion, as is illustrated in FIG. 5. The insulating protection film 52 may alternatively be provided so as to enclose the whole sensor device with the connecting plug portion being left uncovered. Further, the device may be coated with a silica glass layer.

Figure 6:
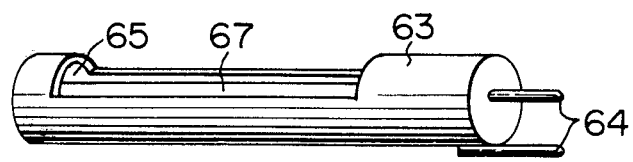

FIG. 6 shows another exemplary structure of the sensor device according to the invention. Referring to this figure, a refractory metallic pipe 63 is used as the refractory metallic supporting base. This embodiment is so constructed that the device shown in FIG. 5 is implemented in the metallic pipe 63 to face externally at a window 67. Subsequently, electrode terminals 64 are mounted, whereby a high temperature sensor device is accomplished. This device is advantageous in that a high mechanical strength against stress as well as external shocks as well as an improved manipulatability are attained due to a cylindrical configuration. As a result of the absence of voids, the sensor device arranged within the pipe 63 as mentioned earlier avoids the problem where the output terminal is overheated or the sensor device body is fatigued with the repetitive stresses applied thereto.

As will be appreciated from the foregoing description, the present invention has provided an improved sensor device which can enjoy an excellent refractory property, a long use life, a high reliability and can be employed for various and numerous practical applications.

Next, the invention will be described in more detail in conjunction with examples.

EXAMPLE 1

A sheet-like material of raw alumina was printed at one surface thereof with electric conductor pattern of tungsten paste and subsequently formed with holes or notches at one end of the sheet material through punching for allowing terminals to be connected to the conductors. Thereafter, the sheet material was wound tightly around a column-like core of raw alumina under pressure so that the electric conductors were interposed between the sheet-like material and the column-like core. The structure thus obtained was fired at a high temperature of 1650° C. in a reducing or an inert gas atmosphere. Then, the terminals of nickel were welded to the electrical conductors by using a fine nickel wire through the notches. The ends of the tungsten conductors exposed at the other end of the structure was applied with a paste of platinum and sintered. A spinel type temperature sensitive element containing 45.81 mol-% of MgO, 4.93 mol-% of NiO, 8.62 mol-% of $Al_2O_3$, 27.09 mol-% of $Cr_2O_3$ and 13.55 mol-% of $Fe_2O_3$ was applied to the platinum-plated conductor ends in a thickness of Ca.-130 μm through a plasma injection process thereby to interconnect the electric conductors by way of the temperature sensitive element which in turn was covered with a protection film of $Al_2O_3$ in a thickness of ca. 270 μm through the flame spraying. The plasma spraying was carried out at a power level of 35 V and 700 A in the gas atmosphere of $N_2$ through a mask from a location spaced from the exposed ends of the conductor by a distance of 70 mm.

The fabricated device is of a structure such as shown in FIG. 1 and has B-constant of about 12,000° K. in a temperature range of 850° to 950° C., resistivity of 540 Ω (at 900° C.). After a heat withstanding test which was effected in a combustion product gas at 1030° C. for 1000 hours, it was found that changes in the characteristics are all within ±3%. No abnormality was found even after vibration withstanding test in which a force of 10 G was applied cyclically 100,000 times.

On the other hand, many of the conventional sensor device in which platinum conductors are embedded in a sintered substrate were subjected to failures at connecting portions due to crystal growth and stress after similar tests.

EXAMPLE 2

An electrically conductive paint of Mo-Mn series was applied to a peripheral surface of a core rod of raw alumina in a conductor pattern through a printing process. After the paint was dried, a paste containing pulverized alumina was applied over the alumina rod. After the paste was dried, the obtained assembly was sintered in a nitrogen gas atmosphere containing 3% of $H_2$ at 1550° C. Both exposed ends of the printed conductors were plated with nickel. Terminal electrodes were welded to the conductors at one end thereof by a high temperature solder, while a temperature sensitive element was provided at the other end of the conductors in the same manner as described hereinbefore in Example 1. Further, a protection film of alumina was applied over the temperature sensitive element in a thickness of 600 μm. Subsequently, only the temperature sensitive end portion of the device was annealed in an electric oven at 950° C. The resistance of thus fabricated sensor device was 550 Ω at 900° C., B-constant was 11,000° K. in a temperature range of 850° C. to 950° C. Excellent characteristics as well as long use life were assured as was in the case of Example 1.

EXAMPLE 3

Electric conductors were formed on a peripheral surface of a sintered rod of alumina by sputtering silicon carbide. Subsequently, a film of alumina was formed around the alumina rod in a film thickness of 50 μm. Nickel was fused through windows formed in the alumina film and terminals for external connection were welded by a high temperature solder. Through windows formed at the other end portion, nickel was applied to the conductors through flame spraying, which was followed by attachment of a temperature sensitive element and application of a protection film as in the case of Example 1. The high temperature sensor device thus fabricated exhibited similar characteristics as the sensor device according to the Example 1.

EXAMPLE 4

Tip sensor portions of the temperature sensor devices fabricated according to Examples 1, 2 and 3 were placed in an electric over held at a temperature of 900° C. to test the heat or environmental condition withstanding capability. Even after having been held at the above temperature in an air atmosphere continuously for 10,000 hours, no change occured in configuration. Variation in B-constant and resistance was within ±1.5%.

EXAMPLE 5

Sensor tip portions of the sensor devices fabricated according to Examples 1, 2 and 3 were inserted in an electric oven held at 900° C. for 15 minutes. Subsequently, the sensor tip portions were taken out from the oven to be cooled rapidly and held at an ambient temperature for 15 minutes, which was followed by re-insertion of the tip portions of the sensor device in the oven to heat them rapidly at 900° C. This rapid heating and cooling cycle was repeated to test the thermal shock withstanding capabilities of the sensor devices. No change was observed in the configuration even after the thermal cycle test had been repeated 4500 times. Variations in B-constant and resistance values remained within ±1.5%.

EXAMPLE 6

The sensor devices fabricated according to Examples 1, 2 and 3 as well as a conventional sensor device in which electrodes formed of platinum wire were embedded and sintered in a temperature sensitive material were placed respectively, in a pipe formed of a heat-resistive alloy and subjected to the thermal cycle test described in Example 5 concurrently with a vibration test using a force of 5 G. Even after the concurrent tests had been repeated for 4000 times, no deformation was observed in the case of the sensor devices fabricated according to Examples 1, 2 and 3. On the other hand, breakage in electrodes and electric connection was found in about 30% of the hitherto known devices.

EXAMPLE 7

A pair of nichrom wires each of 60 mm in length and 1.5 mm in diameter was subjected to sand blasting with pulverized alumina of 200 mesh to roughen the wire surfaces and thereafter applied with alumina particles of 30 μm in particle size through plasma spraying. As the plasma gas, a mixture gas of argon and nitrogen was used. The plasma current was selected at 800 A, while the plasma voltage was maintained at 35 V. The spraying distance was selected at 70 mm. During the injection for a period of several minutes, the pair of nichrom wires were rotated about the longitudinal center axis to form an ellipsoidal column having a long diameter of 6 mm.

The one exposed ends of the paired nichrom wires were used as terminals for external connection, while the other exposed ends of the wires (0.3 mm in length) were attached with a temperature sensitive element in a thickness of ca. 250 μm through plasma spraying in a similar manner as in the case of Example 1. Subsequently, a protection film of 1 mm in thickness was formed of alumina over the temperature sensitive element. The temperature sensitive material was of a spinel component containing 8.6 mol-% of $Al_2O_3$, 50.7 mol-% of MgO, 27.1 mol-% of $Cr_2O_3$ and 13.6 mol-% of $Fe_2O_3$ or $ZrO_2$-series (containing 9 mol-% of $Y_2O_3$).

To remove stress generated upon injection, the fabricated sensor assembly was annealed at 800° C. for 2 hours and cooled to examine the characteristics. The B-constant of the sensors was higher than 10,000° K. in a temperature range of 850° to 950° C. After a heat withstanding test effected in the atmosphere of exhaust gas of a motor vehicle for more than at 1050° for 600 hours, variation in B-constant and resistance values remained within ±3%. Further, a vibration withstanding test using a force of 10 G at a high temperature for 100,000 cycles brought about no appreciable change in the device characteristics.

On the other hand, about 50% of the hitherto known device subjected to the same vibration withstanding test suffered from damage and failure in the junction portion between the sensor conductor and the grounded conductor which is susceptible to damage due to stress.

EXAMPLE 8

One surface of a refractory supporting substrate formed of a plate of Hastelloy having a thickness of 1 mm, a width of 4 mm and a length of 50 mm was subjected to a sand blast using pulverized alumina to be cleaned and finely roughened. Subsequently, the roughened surface was applied with alumina through plasma spraying process using a mask to form a battledorelike planar pattern having a cross-section shown in FIG. 5. As the plasma gas, argon gas was used. The plasma current was maintained at 700 A for an injection gap of about 70 mm. An alumina film was thus formed in thickness of about 100 μm. Subsequently, through a slit-like mask, nichrom conductors having a thickness of 50 μm were formed on the alumina film through plasma flame spraying. Tip ends of nichrom and Hastelloy layers were then plated thin with platinum, which was followed by provision of a temperature sensitive element of a spinel composed of 8.62 mol-% of $Al_2O_3$, 50.74 mol-% of MgO, 27.09 mol-% of $Cr_2O_3$ and 13.55 mol-% of $Fe_2O_3$ or of a $ZrO_2$ series material containing 91 mol-% of $ZrO_2$ and 9 mol-% of $Y_2O_3$ and having a thickness of 150 μm through flame spraying. Finally, a protection film was formed of alumina in thickness of 150 μm under the plasma flame spraying conditions described above to thereby complete a sensor device of a structure shown in FIG. 5.

The sensor device thus obtained has B-constant of about 10,000° K. in a temperature range of 850° C. to 950° C. After the heat withstanding test carried out in the atmosphere of a combustion product gas at 1050° C. for 530 hours, changes in B-constant and resistance value was within ±3%. No variation in characteristics was found after a vibration withstanding test using acceleration of about 10 G at $10^5$ cycles.

In constrast, damages were observed in many of the hitherto known sensor devices undergone the same test at the conductor portions (primarily at platinum wires) and junction which is susceptible to re-crystallization and stress.

EXAMPLE 9

The temperature sensor device fabricated according to Example 8 was coated with an insulating material in thickness of ca. 350 μm over the major and side surfaces to form a protection film through the flame spraying which may be effected by rotating the sensor device around the longitudinal axis thereof.

The protection film may be formed of alumina, magnesia, zirconia or mullite. The plasma spraying was carried out under the same conditions as in the case of Example 7.

The sensor device thus obtained was left in the atmosphere containing 0.1% of nitrogen monooxide and sulfous acid gas, respectively, at 1050° C. for 500 hours. No change was observed in the characteristics of the device. On the other hand, corrosion to some degree was observed in the exposed metallic portions in the case of the sensor device coated with no protection film.

EXAMPLE 10

A pipe of Hastelloy having an outer diameter of 5 mm and an inner diameter of 4 mm was formed with a window and one end of the pipe was tightly closed, as is shown in FIG. 6. A mask bent so as to be closely fitted in the pipe was used to carry out the fusing injection in the same manner as in the case of Example 8. Electrode terminals of nickel each having a diameter of 1 mm were bonded to other end of the pipe and the tips of the terminals were bonded to the conductors directly with nickel. Thereafter, a protection film was formed over the whole window to hermetically close the pipe.

The sensor device thus obtained exhibits excellent characteristics such as those of the sensor device fabricated according the Example 8. Further, the sensor device according to this example is advantageous in that a great mechanical strength can be attained due to the pipe configuration.

EXAMPLE 11

An insulating film was prepared in a similar manner as in the case of Example 8 and a pair of electric conductors were formed on the insulating film extending from the both sides thereof and the one end is connected to the refractory supporting substrate. Both ends meet at a distance from the appear edge of the insulating film which distance corresponds to a quarter of the film length where a sensor element is to be placed. A temperature sensitive element of the composition mentioned in Example 8 which was sintered through a conventional process known in the ceramic industry and cut in a dimension of $3 \times 3 \times 0.2$ mm$^3$ was bonded to the connecting portion by a paste of platinum and fixed. Further, the whole surface of the structure thus obtained was coated with a film of alumina containing 3% of titanium oxide through plasma spraying which was carried out at 800 A and 40 V with a gap of about 45 mm. The porosity of the alumina film was less than 1%. The temperature sensor device as obtained was very stable as in the case of the sensor fabricated according to Example 8.

EXAMPLE 12

Figure 7:
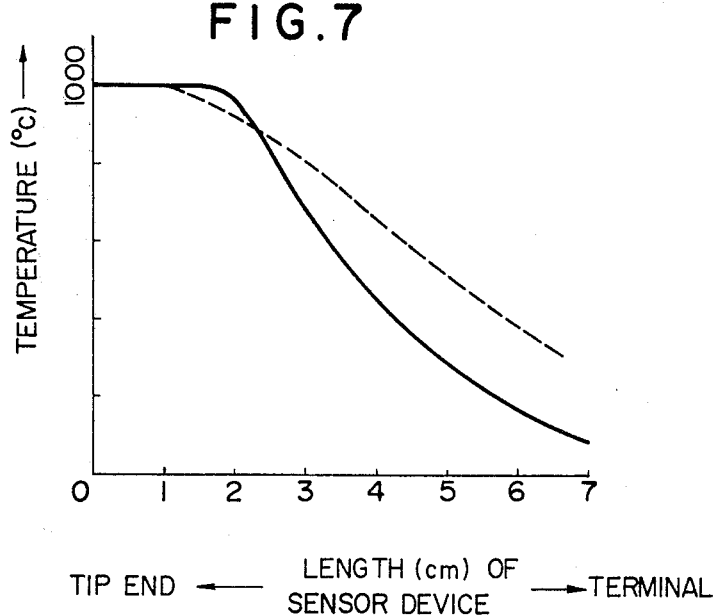
FIG. 7 shows graphically a temperature distribution along the length of a temperature sensor device according to an embodiment of the invention in comparison with that of a hitherto known sensor device.

Temperature distribution of a column-like temperature sensor device fabricated according to Example 1 and having a diameter of 8 mm and a length of 70 mm was measured along the whole length. Sensor tip portion of 20 mm in length of the sensor device was inserted into a pipe-like electric heater to maintain the tip portion at 1000° C., wherein surface temperature of the sensor device was measured. The temperature at the terminals does not exceed 100° C., as is indicated by a solid line curve. On the other hand, a pseudo-sensor of the same configuration was formed of a stainless material or Hastelloy which are used for a temperature sensor for an exhaust box of a motor vehicle and the surface temperature was measured. The temperature at the terminal reaches 300° C. as indicated by a broken-line curve in FIG. 7. Thus, it has been determined that the terminal temperature is far lower than that of the conventional sensor. Similarly, when a cylindrical alumina pipe is inserted into the electrical heater, the surface temperature shows the same temperature distribution as that of the stainless material, thus increasing the terminal temperature of the pipe. In the case of the sensor device according to the invention, the electric heater demands a power of about 400 W, while in the case of the pseudo-sensor device power consumption of the heater amounts to about 550 W, which means that the sensor device according to the invention is excellent in respect of heat loss.

What is claimed is:

1. A sensor device of a ceramic type comprising a sensing element formed of a ceramic material, at least a pair of electric conductors electrically connected to said sensing element and at least two output terminals for connecting said electric conductors with an external circuit, wherein at least one of said paired electric conductors is tightly and closely embedded within an insulating body of a ceramic material except for those portions of said electric conductor at which said conductor is connected to said sensing element, wherein at least one of said output terminals is partially embedded within said insulating body, said insulating body being composed of a voidless solid supporting part and a coating part, said electric conductors being interposed between opposite surfaces of said voidless solid supporting part and said coating part.

2. A sensor device of a ceramic type comprising a sensing element formed of a ceramic material, at least a pair of electric conductors electrically connected to said sensing element and at least two output terminal for connecting said electric conductors with an external circuit, wherein at least one of said paired electric conductors is tightly and closely embedded within an insulating body of a ceramic material except for those portions of said electric conductor at which said conductor is connected to said sensing element, wherein at least one of said output terminals is partially embedded within said insulating body, said insulating body being formed by depositing a ceramic material around said pair of electric conductors through flame spraying.

3. A sensor device according to claim 1, wherein said voidless solid supporting insulation part is of a column-like configuration, and said coating insulation part is in a form of sheet.

4. A sensor device according to claim 1 or 3, wherein said supporting insulation part and said coating insulation part are formed of a raw material which is converted into an insulating material after being fired.

5. A sensor device according to claim 4, wherein at least one of opposite surfaces of the raw materials which constitute said supporting insulation part and said coating insulation part, respectively, is applied with an electrically conductive paint having a heat withstanding capability which is transformed into said electric conductors after having been fired, all of said raw materials and electrically conductive paint are concurrently sintered to thereby constitute an integral structure of the sensor device.

6. A sensor device according to claim 1 or 3, wherein said supporting insulation part is inherently constituted by a sintered insulating material, while said coating insulation part is formed of a raw material which becomes an insulating material after having been fired.

7. A sensor device according to claim 6, wherein at least one of the opposite surfaces of said sintered supporting insulation part and said raw material constituting said coating insulation part after having been fired is applied with a heat-resistive electrically conductive paint which constitutes said electric conductors after having been fired, all of said supporting part, said coating part and said electrically conductive paint being concurrently sintered to constitute an integral structure.

8. A sensor device of a ceramic type comprising a sensing element formed of a ceramic material, at least a pair of electric conductors electrically connected to said sensing element and at least two output terminals for connecting said electric conductors with an external circuit, wherein at least one of said paired electric conductors is tightly and closely embedded within an insulating body of a ceramic material except for those portions of said electric conductor at which said conductor is connected to said sensing element, wherein at least one of said output terminals is partially embedded within said insulating body and wherein at least one of said paired electric conductors is constituted by a heat-resistive metallic substrate on which a layer of an insulating material and a layer of electrically conductive material are successively deposited in this order, said layer of electrically conductive material constituting the other of said paired electric conductors, portion of said layer of insulating material being covered by an insulating material, so that said layer of electrically conductive material is embedded within the insulating mass.

9. A sensor device according to claim 8, wherein said heat-resistive supporting metal substrate is in a form of a pipe, the inner surface of which serves as the substrate surface.

10. A sensor device according to claim 8 or 9, wherein the insulating body is formed through flame spraying.

* * * * *